United States Patent
Aye

(10) Patent No.: US 6,358,269 B1
(45) Date of Patent: Mar. 19, 2002

(54) METHOD OF TREATING PERIPHERAL BRONCHOPLEURAL FISTULAS

(76) Inventor: Ralph Aye, 1221 Madison, #1220, Seattle, WA (US) 98104

( * ) Notice: Subject to any disclaimer, the term of this patent is extended or adjusted under 35 U.S.C. 154(b) by 0 days.

(21) Appl. No.: 09/432,652

(22) Filed: Nov. 2, 1999

Related U.S. Application Data

(60) Provisional application No. 60/106,721, filed on Nov. 2, 1998.

(51) Int. Cl.$^7$ ................................................ A61B 17/04
(52) U.S. Cl. ........................ 606/213; 128/898; 424/443; 424/446
(58) Field of Search ........................ 606/213; 424/443, 424/446; 128/898, 207.15

(56) References Cited

U.S. PATENT DOCUMENTS

| | | | | |
|---|---|---|---|---|
| 3,559,647 A | * | 2/1971 | Bidwell et al. | 604/321 |
| 3,683,913 A | * | 8/1972 | Kurtz et al. | 604/321 |
| 3,782,497 A | * | 1/1974 | Bidwell et al. | 181/233 |
| 4,066,083 A | | 1/1978 | Ries | 128/325 |
| 4,238,480 A | | 12/1980 | Sawyer | 424/177 |
| 4,578,067 A | | 3/1986 | Cruz, Jr. | 604/368 |
| 4,725,671 A | | 2/1988 | Chu et al. | 530/356 |
| 5,024,841 A | | 6/1991 | Chu et al. | 424/422 |
| 5,156,613 A | | 10/1992 | Sawyer | 606/213 |
| 5,206,028 A | | 4/1993 | Li | 424/484 |
| 5,588,424 A | * | 12/1996 | Insler et al. | 128/207.15 |
| 5,660,175 A | * | 8/1997 | Dayal | 128/207.15 |
| 5,669,934 A | * | 9/1997 | Sawyer | 606/213 |
| 5,679,372 A | | 10/1997 | Shimuzu et al. | 424/445 |
| 5,690,675 A | | 11/1997 | Sawyer et al. | 606/229 |
| 5,749,895 A | * | 5/1998 | Sawyer et al. | 606/214 |
| 5,780,048 A | * | 7/1998 | Lee | 424/443 |
| 5,844,016 A | * | 12/1998 | Sawhney et al. | 522/13 |
| 5,900,245 A | * | 5/1999 | Sawhney et al. | 424/426 |
| 5,954,636 A | * | 9/1999 | Schwartz et al. | 600/120 |

* cited by examiner

*Primary Examiner*—Gary Jackson
(74) *Attorney, Agent, or Firm*—Dean A. Craine

(57) ABSTRACT

A method of treating peripheral bronchopleural fistula using a collagen matrix hemostatic pad. The method includes the following steps: (1) selecting a peripheral bronchopleural fistula; (2) selecting a collagen matrix hemostatic pad having sufficient size to cover the fistula; (3) aligning the collagen matrix hemostatic pad completely over the fistula; and (4) securing the collagen matrix hemostatic pad to the tissue sorrounding the fistula.

2 Claims, No Drawings

METHOD OF TREATING PERIPHERAL BRONCHOPLEURAL FISTULAS

This is a utility patent application based on provisional patent application (Ser. No. 60/106,721) filed on Nov. 2, 1998.

BACKGROUND OF THE INVENTION

1. Field of the Invention

This invention relates to improved partial lung resection procedures and more particularly to improved methods of treating peripheral bronchopleural fistulas.

2. Description of the Related Art

In the United States, more than 30,000 lobectomies are performed annually in addition to numerous other partial lung resection procedures including segmentectomy, wedge and bleb resection. Prolonged air leak as a complication of these procedures reportedly occurs in 3–5 of cases. For lobectomies alone, this accounts for more than 1,500 cases per year. Thus, prolonged air leak is a significant cause of patient morbidity and increased hospital cost.

Thoracic procedures including lobectomy, segmentectomy, wedge and bleb resections are all potentially complicated by prolonged air leak. With current surgical technique and postoperative care, it is the duration of these leaks that often dictates the length of hospitalization. Resolution of these leaks sometimes requires invasive measures, adding to patient morbidity and hospital costs. Any reduction in air leak duration shortens hospital stays, reduces morbidity, and decreases overall postoperative expense.

Numerous surgical adhesive materials introduced bronchoscopically, thoracoscopically, or by direct tissue application, have been used in an attempt to control bronchopleural fistulas (BPF). The most commonly investigated materials include cyanoacrylates and fibrin glue sealants. The use of cyanoacrylates requires meticulous tissue preparation and, despite improvements in compound synthesis, concerns with both aldehyde biocompatibility and local inflammatory response still exist. Fibrin glue sealants require autologous cryoprecipitate preparation or risk virally transmitted pathogen exposure, and no commercial product exists to expedite this process. Crosslinked gelatin preparations, methylcellulose hemostatic agents, injectable bovine collagen and various combinations of these materials have also been studied.

What is needed is an approved method of treating peripheral bronchopleural fistulas that does not have the above stated drawbacks.

SUMMARY OF THE INVENTION

It is an object of the invention to provide a method of treating peripheral bronchopleural fistulas It is another object of the invention to provide such a method that hastens the closure of air leaks.

It is a further object of the invention to provide such a method that is relatively easy to perform, and has fewer biocompatibility and inflammatory problems.

These and other objects are met by providing a method of treating peripheral bronchopleural fistulas by applying a collagen matrix hemostatic pad (i.e. INSTAT, sold by Johnson & Johnson Medical, Inc., Arlington, Tex.) over an air leak. The method includes the following steps: (1) selecting a peripheral bronchopleural fistula; (2) selecting a collagen matrix hemostatic pad having sufficient size to cover the fistula; (3) aligning the collagen matrix hemostatic pad completely over the fistula; and (4) attaching the collagen matrix hemostatic pad to the tissue surrounding the fistula.

DESCRIPTION OF THE PREFERRED EMBODIMENT(S)

Disclosed herein is a method of treating peripheral bronchopleural fistulas by applying a collagen matrix hemostatic pad over the fistula. It has been found that the use of a collagen matrix significantly reduces air leaks and decreases patient morbidity.

Clinical Trial

In a preliminary retrospective clinical study using historical controls, it was found that the application of a collagen matrix pad hastens the closure of air leaks and shortens hospital stays. This investigation lacked standardized, controlled comparison groups, preventing definitive conclusions from being drawn. Because of the limitations of this study, we wished to prospectively test this material in a clinically applicable model of pulmonary air leak. No large animal model of peripheral BPF has been reported.

The purpose of this study was to develop such a model, and to determine if the collagen matrix pad could hasten the closure of these air leaks.

Domestic sheep weighing between 41 kg and 66 kg were acclimated in a specially designed 8×4×5 ft pen for at least a one week period prior to enrollment in the study. A total of six "control sheep" underwent the standardized procedure described below. This procedure was then repeated in four more sheep, called "experimental sheep," with the addition of a collagen matrix hemostatic pad applied over the lung defect.

Preoperatively, following placement of an intravenous catheter, both groups of sheep were anesthetized using intravenous ketamine and xylazine, and maintained with isoflurane. Following induction anesthetic and endotracheal intubation, the sheep were placed in a right lateral decubitus position and sheared. Sheep were monitored using an electrocardiographic rhythm strip and continuous oximetery. After sterile prep and draping, a standard left thoracotomy incision between the $4^{th}$ and $5^{th}$ ribs was made, permitting exposure of the apex of the left upper lobe. Serial one-centimeter sections perpendicular to the long axis of the lobe were created using metzenbaum scissors while grasping the lung with non-crushing clamps. Sectioning continued until three bronchioles equal to or greater than one millimeter or two bronchioles equal to or greater than two millimeters were exposed. Sheep with exposed bronchioles greater than four millimeters in diameter were excluded, based on previous data indicating that bronchial diameters greater than five millimeters in diameter were not amenable to endoscopic closure. Meticulous hemostasis was maintained using monopolar electrocautery and every effort was made to evacuate all fluid from the left hemithorax prior to closure.

In the experimental group, a 7.6 cm×10.2 cm collagen matrix hemostatic pad was selected and positioned to the cut surface. The pad was secured over the cut surface using six superficial interrupted 000 chromic sutures, preventing migration of the pad during closure. Two #28F chest tubes were inserted through the $7^{th}$ intercostal space and directed apically, One tube dorsally and one ventrally (dependent in standing position). Chest tubes were secured at two skin sites using heavy, non-absorbable suture. No collagen matrix hemostatic pads were used with the control group of sheep.

In the control group, the average leak duration was 4.92 days (range 3.0–7.0, n=6) with a mean bronchial diameter of 1.85 mm. In the experimental group, the mean duration of air leakage was 1.0 days (range 0.5–1.5, n=4) with a mean bronchial diameter of 2.36 mm. Gross and histologic analysis of the surgical site was performed on three experimental and one control sheep sacrificed at one week, seven months, and nine months, respectively. There was no evidence of accentuated inflammatory response in the experimental group, and late comparisons of control and experimental animals showed no significant differences.

The collagen matrix hemostatic pad used in this experiment is sold under the trademark INSTAT by Johnson & Johnson of Arlington, Tex. The ingredients and components used to manufacture this pad are incorporated by reference herein. It should be understood, however, that other collagen matrix hemostatic pads may be used.

In compliance with the statute, the invention, described herein, has been described in language more or less specific as to structural features. It should be understood, however, the invention is not limited to the specific features shown, since the means and construction shown comprised only the preferred embodiments for putting the invention into effect. The invention is, therefore, claimed in any of its forms or modifications within the legitimate and valid scope of the amended claims, appropriately interpreted in accordance with the doctrine of equivalents.

I claim:

1. A method of treating peripheral bronchopleural fistulas, comprising:
   a. selecting a peripheral bronchopleural fistula;
   b. selecting a collagen matrix hemostatic pad having sufficient size to cover said fistula;
   c. aligning said pad over said fistula; and
   d. securing said pad to the tissue surrounding said fistulas.

2. The method as recited in claim 1, wherein said collagen matrix hemostatic pad is a purified, lyophilized bovine dermal collagen.

* * * * *